United States Patent
Liege et al.

(10) Patent No.: US 11,626,193 B2
(45) Date of Patent: Apr. 11, 2023

(54) MAINTAINING INDIVIDUAL IMMUNIZATION RECORDS

(71) Applicant: MASTERCARD INTERNATIONAL INCORPORATED, Purchase, NY (US)

(72) Inventors: Alexandre Liege, Berkeley, CA (US); Salah Malaika Goss, New York, NY (US); Laura Therese Moll, Chappaqua, NY (US); Henry William Andrew Gillen, Washington, DC (US); Raman Narayanswamy, Pelham, NH (US); Renee Ratay, New York, NY (US); Andreas George Koutsoudis, London (GB)

(73) Assignee: MASTERCARD INTERNATIONAL INCORPORATED, Purchase, NY (US)

( * ) Notice: Subject to any disclaimer, the term of this patent is extended or adjusted under 35 U.S.C. 154(b) by 396 days.

(21) Appl. No.: 16/838,446

(22) Filed: Apr. 2, 2020

(65) Prior Publication Data
US 2020/0321088 A1 Oct. 8, 2020

Related U.S. Application Data

(60) Provisional application No. 62/828,873, filed on Apr. 3, 2019.

(51) Int. Cl.
*G16H 10/60* (2018.01)
*G16H 15/00* (2018.01)
(Continued)

(52) U.S. Cl.
CPC ............ *G16H 10/60* (2018.01); *G06F 16/23* (2019.01); *G06F 21/32* (2013.01); *G16H 15/00* (2018.01); *G16H 20/10* (2018.01)

(58) Field of Classification Search
None
See application file for complete search history.

(56) References Cited

U.S. PATENT DOCUMENTS

| 8,234,125 B2 * | 7/2012 | Skocic | G16H 80/00 340/5.83 |
| 2011/0029488 A1 * | 2/2011 | Fuerst | G16H 30/20 707/636 |

(Continued)

FOREIGN PATENT DOCUMENTS

JP   2005217923 A   *   8/2005

OTHER PUBLICATIONS

Waterloo region students face suspension for incomplete vaccination records.(Mar. 1, 2019). Times. Retrieved from https://dialog.proquest.com/professional/docview/2187252551?accountid=131444 (Year: 2019).*

(Continued)

*Primary Examiner* — Rachel L. Porter
(74) *Attorney, Agent, or Firm* — Michael Best & Friedrich LLP

(57) ABSTRACT

A system for maintaining individual immunization records. The system includes a tracking vehicle storing a first instance of a user record a terminal including an electronic processor and a memory. The electronic processor is configured to communicate with the tracking vehicle, obtain a second instance of the user record stored in the memory of the terminal and determine whether immunization data in the first instance or the second instance is more recent. When the first instance of the user record from the tracking vehicle includes more recent immunization data than the second instance of the user record stored in the memory, the electronic processor is configured to update the user record stored in the memory of the terminal with the more recent (Continued)

immunization data in the first instance of the user record of the tracking vehicle.

12 Claims, 15 Drawing Sheets

(51) Int. Cl.
*G06F 16/23* (2019.01)
*G06F 21/32* (2013.01)
*G16H 20/10* (2018.01)

(56) References Cited

U.S. PATENT DOCUMENTS

| | | | |
|---|---|---|---|
| 2011/0131055 A1* | 6/2011 | Grady | G16H 10/60 |
| | | | 705/2 |
| 2013/0110778 A1* | 5/2013 | Taylor | G06F 11/1435 |
| | | | 707/624 |
| 2016/0283666 A1* | 9/2016 | Kutscher | G16Z 99/00 |
| 2016/0342744 A1 | 11/2016 | Joao | |
| 2018/0197143 A1 | 7/2018 | Daub et al. | |
| 2018/0233225 A1* | 8/2018 | Experton | G16H 10/60 |

OTHER PUBLICATIONS

International Search Report and Written Opinion for Application No. PCT/US2020/026380 dated Jul. 2, 2020 (6 pages).

* cited by examiner

FIG. 5

USER RECORD

Birth registration information
First name
Last name
Sex
Child's DOB
Child's age
Birth weight (kg)
Neonatal Tetanus Protection
Child's home health facility
Child's register number
Child's Vaccination ID
Mother/guardian first name
Mother/guardian last name
Mother/guardian DOB
Mother/guardian phone number
Second guardian phone number
Child's commune
Other commune
Home address
Preferred Language

Growth Monitoring Data
Weight (kg)
Date
Age

Vaccination Data
Name of vaccination administered
Date vaccination administered

Vitamin Data
Name of type of vitamin A administered
Date vitamin A administered

Death Information
Date of death
Suspected cause of death
Where death occured

Adverse Event Information
Name of Vaccine patient reacted to
AEFI Form Completed

705 — COMMUNICATE WITH THE TRACKING VEHICLE

710 — OBTAIN A SECOND INSTANCE OF THE USER RECORD STORED IN THE FIRST MEMORY OF THE TERMINAL

715 — DOES THE FIRST INSTANCE OF THE USER RECORD FROM THE TRACKING VEHICLE INCLUDE MORE RECENT IMMUNIZATION DATA THAN THE SECOND INSTANCE OF THE USER RECORD STORED IN THE FIRST MEMORY?

YES

720 — UPDATE THE USER RECORD STORED IN THE FIRST MEMORY OF THE TERMINAL WITH THE MORE RECENT IMMUNIZATION DATA IN THE FIRST INSTANCE OF THE USER RECORD OF THE TRACKING VEHICLE

NO

725 — RECEIVE UPDATED IMMUNIZATION INFORMATION FROM A CLINICIAN WHEN THE CLINICIAN PROVIDES A NEW IMMUNIZATION TO THE USER BASED UPON THE INSTANCES OF THE USER RECORD FROM THE TRACKING VEHICLE AND TERMINAL

730 — UPDATE THE FIRST AND SECOND INSTANCES OF THE USER RECORDS TO REFLECT THE NEW IMMUNIZATION

735 — COMMUNICATE USER RECORD UPDATES WITH A SERVER WHEN CONNECTIVITY WITH THE SERVER IS ESTABLISHED

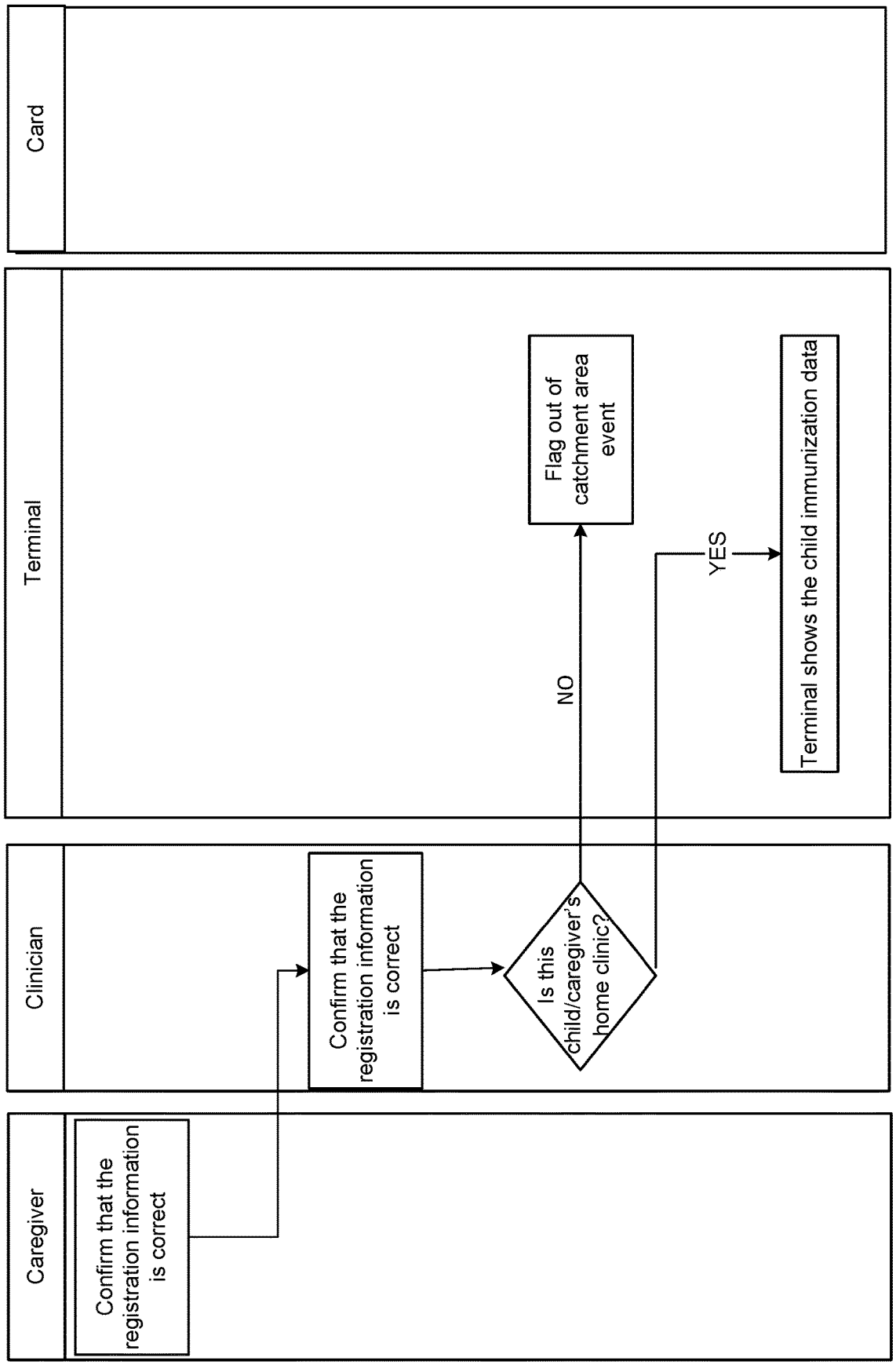

FIG. 10

| # | Name | Date | Gender | <S> | Telephone | BCG | Hep B | Polio Oral 0 | Rotor Oral 1 | Pneumo 1 | Penta 1 | Rota virus 1 | Polio Oral 2 | Pneumo 2 | Penta 2 | Rota Virus 2 | Polio Oral 3 | Pneumo 3 | Penta 3 | Meas A | VAA | MR1 | MR2 |
|---|---|---|---|---|---|---|---|---|---|---|---|---|---|---|---|---|---|---|---|---|---|---|---|
| 1 | Mukisa, A | 2/02/2021 | F | A | 0200 5252 12 | 2/02 2019 | 2/02 2019 | 2/02 2019 | 2/02 2019 | 2/02 2019 | 2/02 2019 | 2/02 2019 | 2/02 2019 | 2/02 2019 | 2/02 2019 | 2/02 2019 | 2/02 2019 | 2/02 2019 | 2/02 2019 | 2/02 2019 | | 2/02 2019 | 2/02 2019 |
| 2 | Kioga, B | 2/02/2019 | M | A | 0223 5252 12 | 2/02 2019 | 2/02 2019 | 2/02 2019 | 2/02 2019 | 2/02 2019 | 2/02 2019 | 2/02 2019 | 2/02 2019 | 2/02 2019 | 2/02 2019 | 2/02 2019 | 2/02 2019 | 2/02 2019 | 2/02 2019 | | | | |
| 3 | Nakoora, C | 2/02/2019 | F | A | 0223 5252 13 | 2/02 2019 | 2/02 2019 | 2/02 2019 | 2/02 2019 | 2/02 2019 | 2/02 2019 | 2/02 2019 | 2/02 2019 | 2/02 2019 | | | | | | 2/02 2019 | | | |
| 4 | Bagoole, D | 2/02/2019 | M | A | 0223 5252 15 | 2/02 2019 | 2/02 2019 | 2/02 2019 | 2/02 2019 | 2/02 2019 | 2/02 2019 | 2/02 2019 | 2/02 2019 | 2/02 2019 | | | | | | | | | |
| 5 | Masera, E | 2/02/2019 | M | A | 0224 5252 16 | 2/02 2019 | 2/02 2019 | 2/02 2019 | 2/02 2019 | 2/02 2019 | 2/02 2019 | 2/02 2019 | | 2/02 2019 | | | | | | | | | |
| 6 | Hakim, F | 2/02/2019 | M | A | 0224 5252 17 | 2/02 2019 | 2/02 2019 | 2/02 2019 | 2/02 2019 | 2/02 2019 | 2/02 2019 | | 2/02 2019 | 2/02 2019 | 2/02 2019 | 2/02 2019 | | | | | | | |
| 7 | Aakiiki, G | 2/02/2019 | M | A | 0225 5252 18 | 2/02 2019 | 2/02 2019 | 2/02 2019 | 2/02 2019 | 2/02 2019 | | | | 2/02 2019 | 2/02 2019 | 2/02 2019 | | | | | | | |
| 8 | Abdalla, H | 2/02/2019 | M | A | 0225 5252 19 | 2/02 2019 | 2/02 2019 | 2/02 2019 | 2/02 2019 | | | | | | | | 2/02 2019 | | | | | | |
| 9 | Hashima, I | 2/02/2019 | M | A | 0226 5252 19 | 2/02 2019 | 2/02 2019 | 2/02 2019 | 2/02 2019 | | | | | | | | | | | | | | |

1000

MAINTAINING INDIVIDUAL IMMUNIZATION RECORDS

RELATED APPLICATIONS

This application claims priority to U.S. Provisional Patent Application No. 62/828,873, filed Apr. 3, 2019, the entire content of which is hereby incorporated by reference.

BACKGROUND

In some counties, the frequent movement of people makes the recording of birth and the corresponding issuance of birth certificates as well as the timely and accurate recording of immunizations difficult. In the absence of a birth certificate and of a well-maintained vaccination record, there is no reliable method of estimating the size of the population that needs to get vaccinated, or verifying whether a child has already received an immunization. These issues can lead to misallocation of resources (for example, vaccine doses and staff), redundant administration of vaccines, and flawed estimates of immunization coverage. Collectively, these issues make it difficult to protect a population from communicable diseases.

In order for children to be fully immunized, their caregivers need to bring them to an immunization center five times. In some regions, the reported drop-out rate is high, mainly due to a lack of awareness of the immunization schedule and a high cost of transportation to travel to clinics to get immunized.

Issues that plague governments and organizations seeking to immunize populations include, a lack of connectivity in remote areas false claims, a high cost of processing data due to a heavy reliance on paper based forms, poor quality of data due to inaccuracy caused by using paper based records, and the like.

SUMMARY

Embodiments herein provide tracking vehicles to patients and terminals to clinics that eliminate the need for paper based records and consistent connectivity. Immunization data and unique identifiers may be stored on the tracking vehicles. Terminals at clinics are able to read and update information stored on the tracking vehicles without being connected to a server. However, the terminals are able to connect to a communication network to send and receive information to/from a server when a connection to the server becomes available. In some embodiments, each tracking vehicle is associated with a user and the user has access to a financial account which can be used to pay for, for example, transportation to a clinic. In other embodiments, each tracking vehicle is associated with a user (for example, a child) and a caregiver (for example, the child's guardian) and the caregiver has access to a financial account. Financial value may also be added to the financial account. For example, a financial award may be added to the financial account when a user receives an immunization to incentivize caregivers to immunize children.

One example embodiment describes a system for maintaining individual immunization records. The system includes a tracking vehicle storing a first instance of a user record and a terminal including an electronic processor and a memory. The electronic processor is communicatively connected to the memory. The electronic processor is configured to communicate with the tracking vehicle, obtain a second instance of the user record stored in the memory of the terminal and determine whether immunization data in the first instance or the second instance is more recent. When the first instance of the user record from the tracking vehicle includes more recent immunization data than the second instance of the user record stored in the memory, the electronic processor is configured to update the user record stored in the memory of the terminal with the more recent immunization data in the first instance of the user record of the tracking vehicle. The electronic processor is also configured to receive updated immunization information from a clinician when the clinician provides a new immunization to the user based upon the instances of the user record from the tracking vehicle and terminal, update the first and second instances of the user records to reflect the new immunization, and communicate user record updates with a server when connectivity with the server is established.

Another embodiment describes a method for maintaining individual immunization records. The method includes a terminal including an electronic processor and a memory communicating with a tracking vehicle storing a first instance of a user record, obtaining, with the electronic processor, a second instance of the user record stored in the memory of the terminal, and determining, with the electronic processor, whether immunization data in the first instance or the second instance is more recent. When the first instance of the user record from the tracking vehicle includes more recent immunization data than the second instance of the user record stored in the memory of the terminal, the method includes updating the user record stored in the memory of the terminal with the more recent immunization data in the first instance of the user record of the tracking vehicle. The method further includes receiving updated immunization information from a clinician when the clinician provides a new immunization to the user based upon the instances of the user record from the tracking vehicle and terminal, updating the first and second instances of the user records to reflect the new immunization, and communicating user record updates with a server when connectivity with the server is established.

Yet another example embodiment describes, a non-transitory computer-readable medium with computer-executable instructions stored thereon executed by an electronic processor to perform the method maintaining individual immunization records. The method includes a terminal including an electronic processor and a memory communicating with a tracking vehicle storing a first instance of a user record, obtaining, with the electronic processor, a second instance of the user record stored in the memory of the terminal, and determining, with the electronic processor, whether immunization data in the first instance or the second instance is more recent. When the first instance of the user record from the tracking vehicle includes more recent immunization data than the second instance of the user record stored in the memory of the terminal, the method includes updating the user record stored in the memory of the terminal with the more recent immunization data in the first instance of the user record of the tracking vehicle. The method further includes receiving updated immunization information from a clinician when the clinician provides a new immunization to the user based upon the instances of the user record from the tracking vehicle and terminal, updating the first and second instances of the user records to reflect the new immunization, and communicating user record updates with a server when connectivity with the server is established.

Before any embodiments are explained in detail, it is to be understood that the embodiments are not limited in its application to the details of the configuration and arrangement of components set forth in the following description or illustrated in the accompanying drawings. The embodiments are capable of being practiced or of being carried out in various ways. Also, it is to be understood that the phraseology and terminology used herein are for the purpose of description and should not be regarded as limiting. The use of "including," "comprising," or "having" and variations thereof are meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings.

In addition, it should be understood that embodiments may include hardware, software, and electronic components or modules that, for purposes of discussion, may be illustrated and described as if the majority of the components were implemented solely in hardware. However, one of ordinary skill in the art, based on a reading of this detailed description, would recognize that, in at least one embodiment, any electronic-based aspects may be implemented in software (e.g., stored on non-transitory computer-readable medium) executable by one or more processing units, such as a microprocessor and/or application specific integrated circuits ("ASICs"). As such, it should be noted that a plurality of hardware and software based devices, as well as a plurality of different structural components, may be utilized to implement the embodiments. For example, "servers" and "computing devices" described in the specification can include one or more processing units, one or more computer-readable medium modules, one or more input/output interfaces, and various connections (e.g., a system bus) connecting the components.

Other aspects of the embodiments will become apparent by consideration of the detailed description and accompanying drawings.

BRIEF DESCRIPTION OF THE DRAWINGS

FIG. 5 illustrates an example of a user record according to some embodiments.

FIG. 7 illustrates a method for maintaining individual immunization records according to some embodiments.

FIGS. 9A through 9D illustrate an example flowchart of the functionality performed the system of FIG. 1 when a user and caregiver make a subsequent visit to a clinic but do not provide biometric information.

FIG. 10 illustrates an example table of immunization information for a plurality of patients for which the terminal of FIG. 2 stores a plurality of user records.

DETAILED DESCRIPTION

Figure 1:
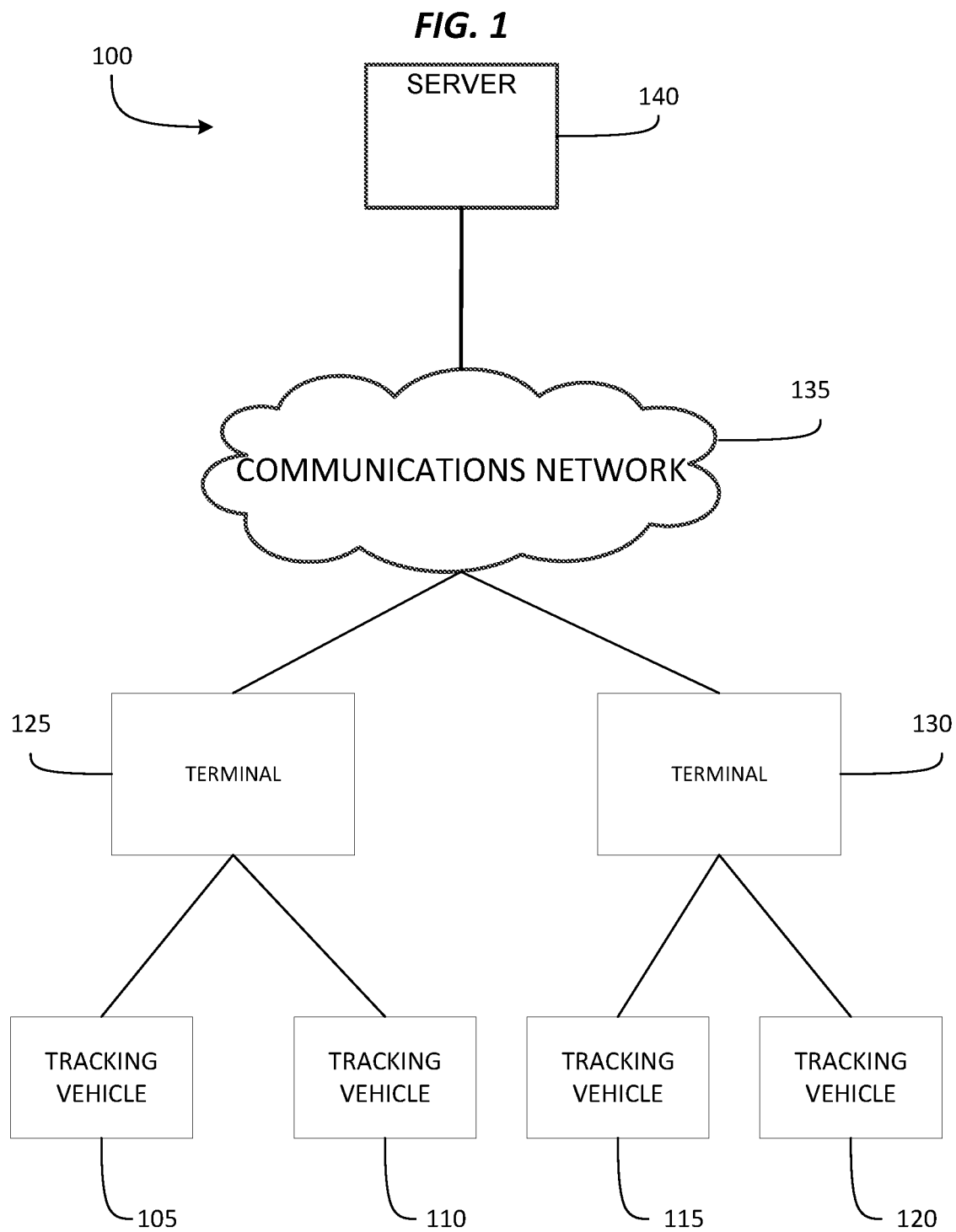
FIG. 1 illustrates a system for maintaining individual immunization records according to some embodiments.

FIG. 1 illustrates a system 100 for maintaining individual immunization records. It should be noted that immunization records may be referred to herein as user records and that these user records include immunization data associated with a particular user or patient. In embodiments, the system 100 includes a plurality of tracking vehicles 105-120, a plurality of terminals 125-130, a communication network 135, and a server-side mainframe computer or server 140. In some embodiments, the plurality of tracking vehicles 105-120 are, for example, plastic cards that include a magnetic strip or a computer readable chip. In other embodiments, the plurality of tracking vehicles 105-120 are, for example, mobile devices including an application configured to securely store a user record. Each of the terminals 125-130 are configured to communicate with the tracking vehicles 105-120 via, for example, the magnetic strip, computer chip, and/or a communication network similar to the communication network 135. Each of the terminals 125-130 are configured to communicatively connect to the server 140 through the communication network 135 and provide information to the server 140 related to the immunization records stored on the terminals 125-130. Each of the terminals 125-130 in the system 100 is associated with a clinic and more than one terminal may be associated with a clinic. Portions of the wireless communication network 135 may be implemented using a wide area network, such as the Internet, a local area network, such as a Bluetooth™ network or Wi-Fi, and combinations or derivatives thereof. It should be understood that each server included in the system 100 may communicate with any number of terminals, and the two terminals 125 and 130 illustrated in FIG. 1 are purely for illustrative purposes. Similarly, it should also be understood that the system 100 may include any number of servers and the single server 140 illustrated in FIG. 1 is purely for illustrative purposes. Similarly, it should also be understood that the system 100 may include any number of tracking vehicles and the four tracking vehicles 105-120 illustrated in FIG. 1 is purely for illustrative purposes. Also, in some embodiments, one of the terminals 125 and 130 may communicate with the server 140 through one or more intermediary devices (not shown).

The system 100 is configured to allow the terminals 125-130 to be mobile and be operated in remote areas. The terminals 125-130 are able to operate in remote areas because they do not need to be in communication with the server 140 to be operated. The terminals 125-130 may only communicate with the server 140 when the terminals 125-130 are within range of a communication network (for example, the communication network 135) via which they connect to the server 140. The terminals 125-130 do not always have to be in communication with the server 140 because each user possesses a tracking vehicle that includes an up to date immunization record for the user and the terminals 125-130 can communicate with the tracking vehicles 105-120 whether or not the terminals 125-130 are in communication with the server 140. Thus, this advantageously allows the terminals of an immunization network to effectively be used in multiple locations while speeding up the process of what otherwise would be a slower and more cumbersome (or non-existent) reconciliation process of multiple different immunization records on multiple different electronic devices and associated with different location, different times, or both.

Figure 2:
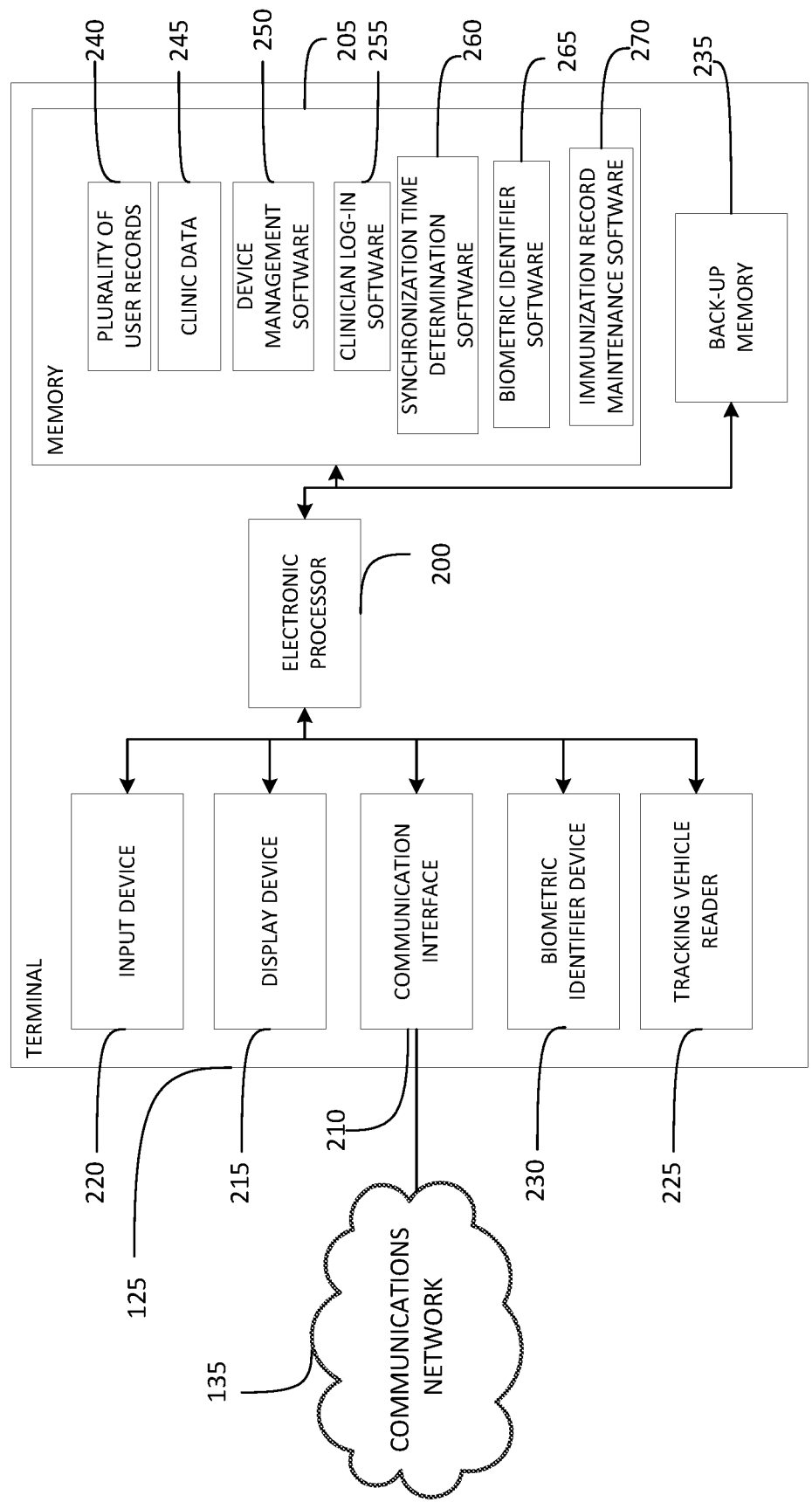
FIG. 2 illustrates a terminal of the system of FIG. 1 according to some embodiments.

FIG. 2 illustrates one embodiment of the terminal 125 of the system 100. The terminal 125 may be, for example, an electronic device, such as a smart phone, a smart watch, a tablet computer, a laptop computer, mixed reality headsets, or the like. The terminal 125 illustrated in FIG. 2 includes an electronic processor 200 (for example, a microprocessor, application-specific integrated circuit (ASIC), or another suitable electronic device), a memory 205 (for example, a non-transitory, computer-readable storage medium), and a communication interface 210 such as a transceiver, for communicating over the communication network 135 and, optionally, one or more additional communication networks or connections.

As illustrated in FIG. 2, the terminal 125 also includes a display device 215, an input device 220, a tracking vehicle reader 225, a biometric identifier device 230, and a back-up memory 235. The display device 215 may be, for example, a touchscreen, a liquid crystal display ("LCD"), a light-emitting diode ("LED") display, an organic LED ("OLED") display, an electroluminescent display ("ELD"), and the like. The input device 220 may be, for example, a keypad, a mouse, a touchscreen (for example, as part of the display device 215), a microphone, a camera, or the like. The tracking vehicle reader 225 may be, for example, a magnetic strip reader, a chip reader, a Radio-frequency identification ("RFID") reader such as a near-field communications (NFC) reader, or the like. The biometric identifier device 230 may be, for example, a fingerprint scanner, a retinal scanner, a camera, a combination of the foregoing, or the like. The back-up memory 235 may be, for example, a non-transitory, computer-readable storage medium that may be removed from the terminal 125, such as a secure digital (SD) card or the like.

The electronic processor 200, the memory 205, the communication interface 210, the display device 215, the input device 220, the tracking vehicle reader 225, the biometric identifier device 230, and the back-up memory 235 communicate wirelessly, over one or more communication lines or buses, or a combination thereof. It should be understood that the terminal 125 may include additional components than those illustrated in FIG. 2 in various configurations and may perform additional functionality than the functionality described in the present application. Also, it should be understood that, although not described or illustrated herein, the terminal 130 may include similar components and perform similar functionality as the terminal 125.

As illustrated in FIG. 2, the memory 205 of the terminal 125 includes a plurality of user records 240, clinic data 245, device management software 250, clinician log-in software 255, synchronization time determination software 260, biometric identifier software 265, and immunization record maintenance software 270. It should be understood that the memory 205 may store additional applications and data and the applications and data stored in the memory 205 may be stored on multiple memory devices or modules. Also, in some embodiments, the functionality described herein as being provided by the device management software 250, the clinician log-in software 255, and the synchronization time determination software 260, the biometric identifier software 265, and the immunization record maintenance software 270 may be distributed and combined in various configurations. For example, the functionality provided by the immunization record maintenance software 270 be divided among multiple different applications. In another example, the functionality described as being performed by the immunization record maintenance software 270 and the synchronization time determination software 260 may be combined in a single software application.

In some embodiments, the device management software 250 is configured to limit the functionality of the terminal 125 to the functions necessary to the operation of a clinic. For example, the device management software 250 may delete or disable applications pre-installed on the terminal 125 that do not need to be executed to maintain individual immunization records.

The clinician log-in software 255 is configured to grant a clinician access to the plurality of user records 240 and the clinic data 245, upon receiving correct log-in credentials. The clinician log-in software 255 also includes the log-in information of those clinicians associated with the terminal 125.

The synchronization time determination software 260 tracks when the terminal 125 last communicated with the server 140 via the communication network 135. For example, the synchronization time determination software 260 may record a time, start a timer, or both when the terminal 125 communicates with the server 140. In some embodiments, when a predetermined amount of time has passed since the terminal 125 communicated with the server 140, the synchronization time determination software 260 is configured to disable the terminal 125.

The electronic processor 200, when executing the biometric identifier software 265, is configured to receive data from the biometric identifier device 230 and, in the case of caregivers and users, determine if the received data matches biometrically derived identifier information received from a tracking vehicle (for example, the tracking vehicle 105) in order to verify a caregiver's or user's identity or, in the case of a clinician's, determine if the received data matches a biometrically derived identifier information stored on a terminal or a tracking vehicle to allow a clinician to log on to or assess a terminal (for example, the terminal 125). For example, the biometric identifier software 265 may include facial recognition software which identifies a face in an image from the biometric identifier device 230 (in this case, a camera). The electronic processor 300, when executing the biometric identifier software 265, matches the identified face to the facial data stored on the tracking vehicle 105, the terminal 125, or on the server 140. In some embodiments, the biometric identifier software 265 includes, in addition to or instead of facial recognition software, palm recognition software, fingerprint recognition software, both, or the like. In some embodiments, rather than matching a received biometric identifier of the user or caregiver to biometrically derived identifier information stored on the tracking vehicle 105, the memory 205 includes software for matching a password or pin received via the input device 220 to a pin or password received from the tracking vehicle 105. In some embodiments, rather than matching a received biometric identifier of a clinician to biometrically derived identifier information stored in the memory 205 of the terminal 125 or on the tracking vehicle 105, the memory 205 includes software for matching a password or pin received via the input device 220 to a pin or password stored in the memory 205 of the terminal 125.

The immunization record maintenance software 270 is configured to update the plurality of user records 240 and clinic data 245 based on information received from the server 140, the tracking vehicles 105-120, and, via the input device 220, the clinician. For example, the immunization record maintenance software 270, when executed by the electronic processor 200, is configured to perform the functionality described in the method 700 which will be described in more detail below with regards to FIG. 7.

Figure 3:
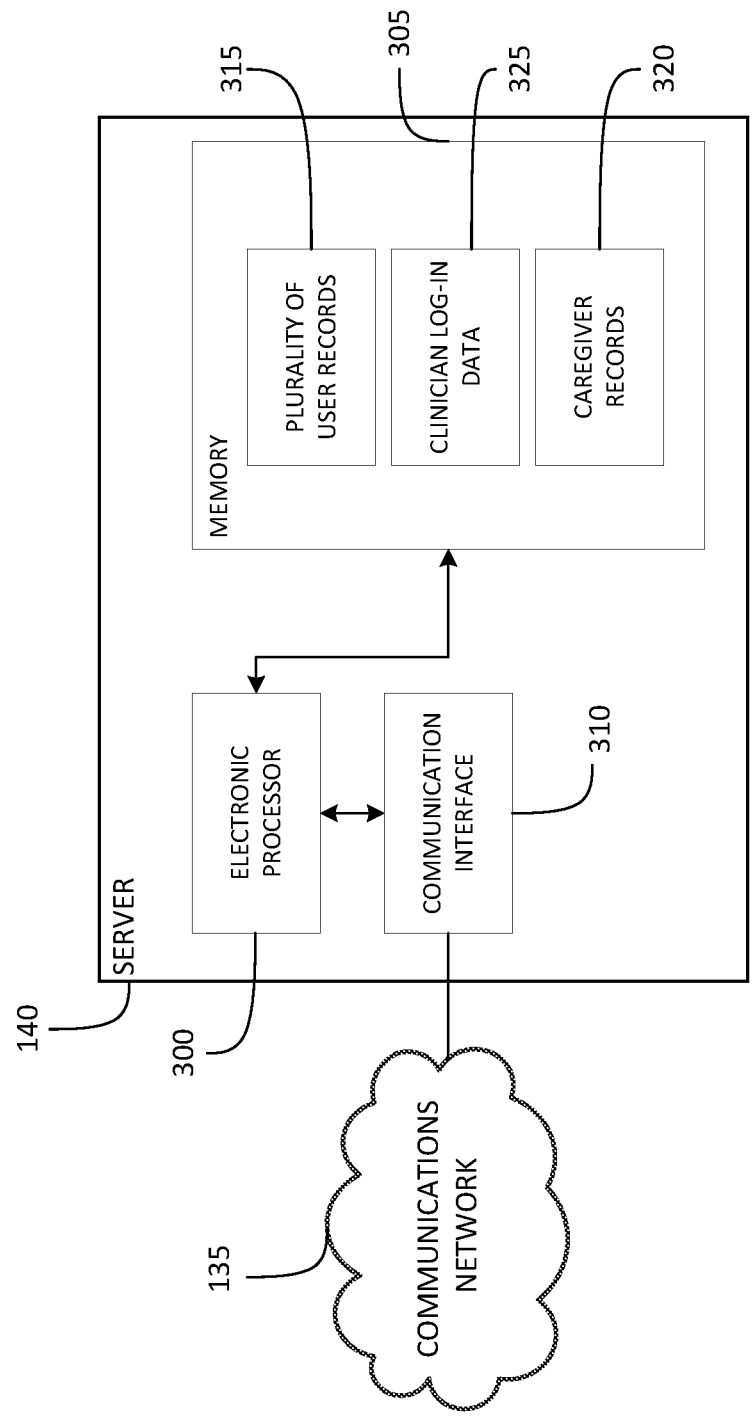
FIG. 3 illustrates a server of the system of FIG. 1 according to some embodiments.

FIG. 3 illustrates one embodiment of the server 140 of the system 100. The server 140 illustrated in FIG. 3 includes a electronic processor 300 (also described herein as a server electronic processor 300) (for example, a microprocessor, application-specific integrated circuit (ASIC), or another suitable electronic device), a memory 305 (also described herein as the server memory 305) (for example, a non-transitory, computer-readable storage medium), and a communication interface 310 such as a transceiver, for communicating over the communication network 135 and, optionally, one or more additional communication networks or connections. The electronic processor 300, the memory 305, and the communication interface 310 communicate wirelessly, over one or more communication lines or buses, or a combination thereof. It should be understood that the server 140 may include additional components than those illustrated in FIG. 3 in various configurations and may perform additional functionality than the functionality described in the present application.

As illustrated in FIG. 3, the memory 305 of the server 140 includes a plurality of user records 315, a plurality of caregiver records 320, and clinician log-in data 325 received from the terminals 125 and 130 included in the system 100. It should be understood that the memory 305 may store additional applications and data and the applications and data stored in the memory 305 may be stored on multiple memory devices or modules.

Figure 4:
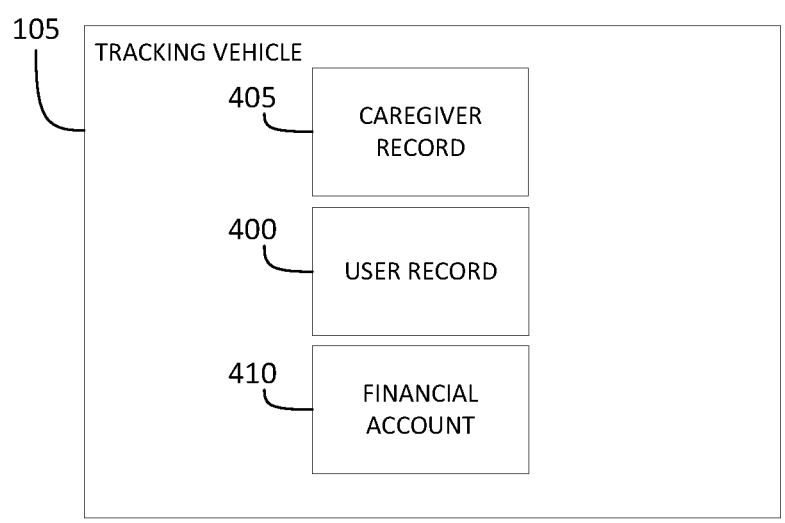
FIG. 4 illustrates a tracking vehicle of the system of FIG. 1 according to some embodiments.

FIG. 4 illustrates an example of the tracking vehicle 105 of the system 100. In some embodiments, the tracking vehicle 105 stores a user record 400, a caregiver record 405, a financial account 410, a combination of the foregoing, and the like. The tracking vehicle may include, for example, a chip, a magnetic strip, or the like that the tracking vehicle reader 225 is configured to receive information from. An example of the data that is stored in the user record 400 (and may be stored in one of the user records of the plurality of user records 315 or the plurality of user records 240) is illustrated in FIG. 5. As illustrated in FIG. 5 the user record includes patient information and caregiver information. It should be understood that a user record may include more, less, or different information or data than that which is illustrated in FIG. 5.

Figure 6:
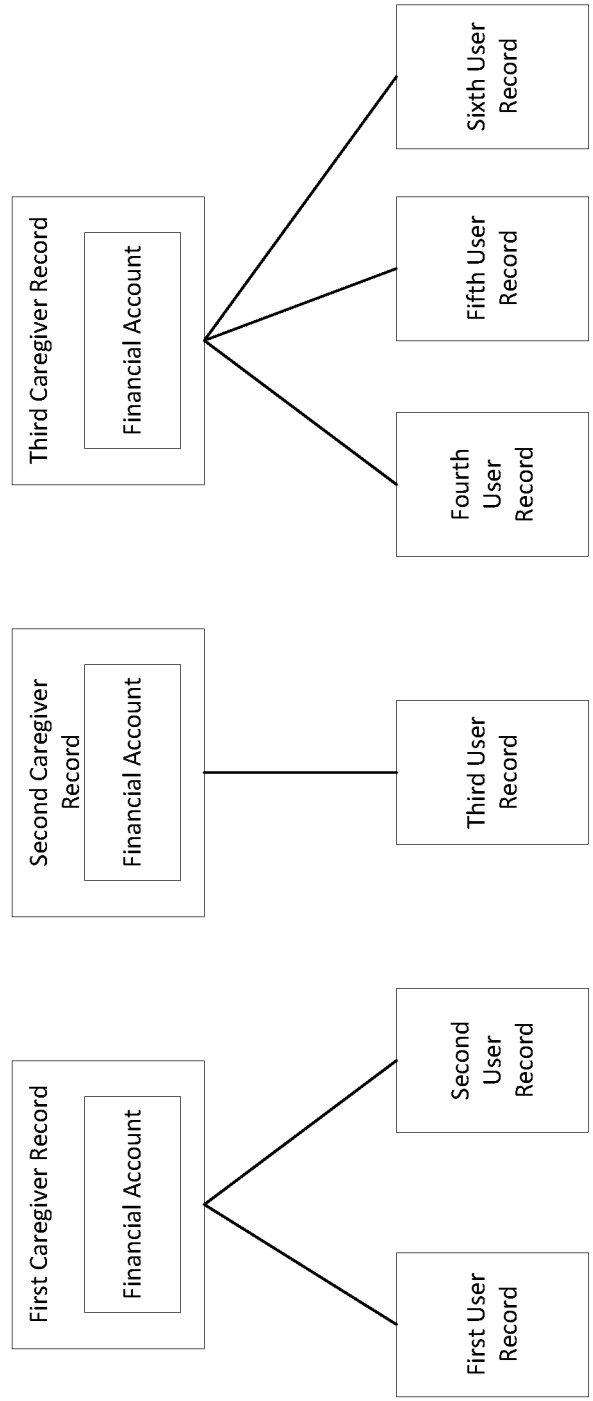
FIG. 6 illustrates an example of the relationships between user records, caregiver records, and financial accounts according to some embodiments.

FIG. 6 illustrates example relationships between user records, caregiver records, and financial accounts. In the example illustrated in FIG. 6 each user record is associated with a single caregiver record through a unique caregiver identifier but each caregiver record (or unique caregiver identifier) may be associated with one or more user records. Additionally, each caregiver record (or unique caregiver identifier) is associated with a single financial account that a caregiver may have access to in order to, for example, pay for treatment at a clinic or pay for transportation to a clinic.

FIG. 7 illustrates an example method 700 of maintaining individual immunization records. At step 705, the terminal 125 communicates with a tracking vehicle (for example, the tracking vehicle 105). In some embodiments, the terminal 125 receives a first instance of a user record from the tracking vehicle 105. At step 710, the electronic processor 200 obtains a second instance of the user record from the memory 205 of the terminal 125. At step 715, the electronic processor 200 determines if the first instance of the user record from the tracking vehicle 105 includes more recent immunization data than the second instance of the user record stored in the memory 205. For example, the electronic processor 200 may compare which instance has a more recent time stamp or the electronic processor 200 may determine which instance includes more data. At step 720, when the first instance of the user record from the tracking vehicle 105 includes more recent immunization data than the second instance of the user record stored in the memory 205, the electronic processor 200 updates the user record stored in the memory 205 of the terminal 125 with the more recent immunization data in the first instance of the user record of the tracking vehicle 105. At step 725, the electronic processor 200 receives updated immunization information from a clinician when the clinician provides a new immunization to the user based upon the instances of the user record from the tracking vehicle 105 and terminal 125. For example, the electronic processor 200 may receive input data regarding administered vaccinations from a clinician via the input device 220. At step 730, the electronic processor 200 updates the first and second instances of the user records to reflect the new immunization. In some embodiments, at step 735, the terminal 125 communicates user record updates with the server 140 when connectivity with the server is established. For example, when the terminal 125 is connected to the communication network 135 and in communication with the server 140, the electronic processor 200 receives a third instance of the user record from the server 140. When the third instance of the user record from the server 140 includes more recent immunization data than the second instance of the user record stored in the memory 205, update the user record stored in the memory 205 of the terminal 125 with the more recent immunization data in the third instance of the user record from the server 140. This situation can occur when, e.g., the user associated with the user record received a recent immunization in association with, e.g., terminal 130, and terminal 130 had updated its information to server 140 prior to terminal 125 coming into communication with server 140.

In some embodiments, the plurality of user records 240 included in the memory 205 are periodically saved to the back-up memory 235. In some embodiments, when the terminal 125 is communicatively connected to the server 140, the server 140 may check that a user record included in the memory 205 or back-up memory 235 of the terminal 125 has been successfully stored in the memory 305 and if at least a predetermined amount of time has passed since the last update to the user record occurred. If the predetermined amount of time has passed and the user record has been successfully stored, the server 140 may send a signal to the terminal 125 indicating that the user record may be deleted from the memory 205 and the back-up memory 235.

Figure 8A:
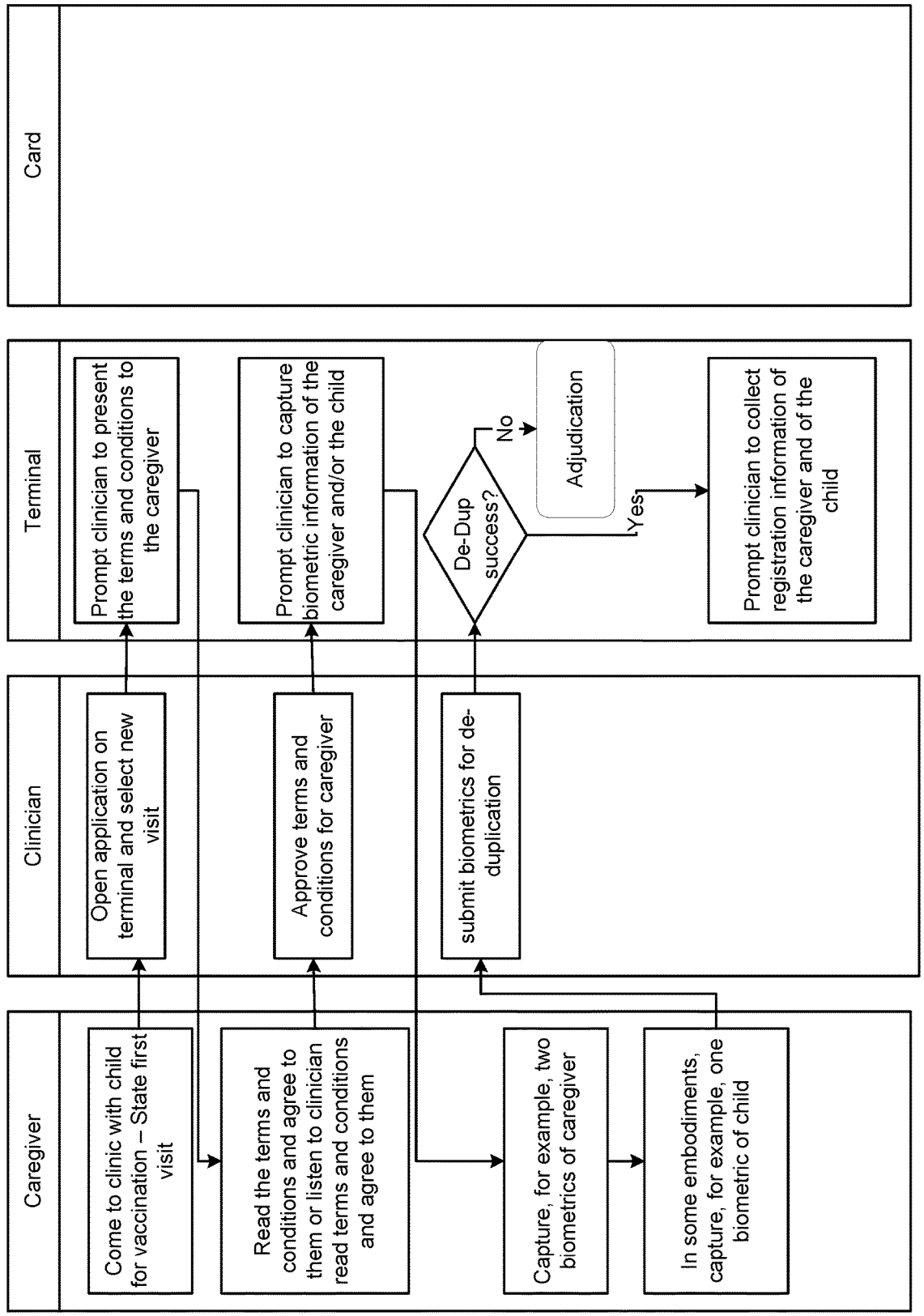
FIGS. 8A and 8B illustrate an example flowchart of the functionality performed by the system of FIG. 1 when a user and caregiver visit a clinic for the first time and provide biometric information.
Figure 8B:
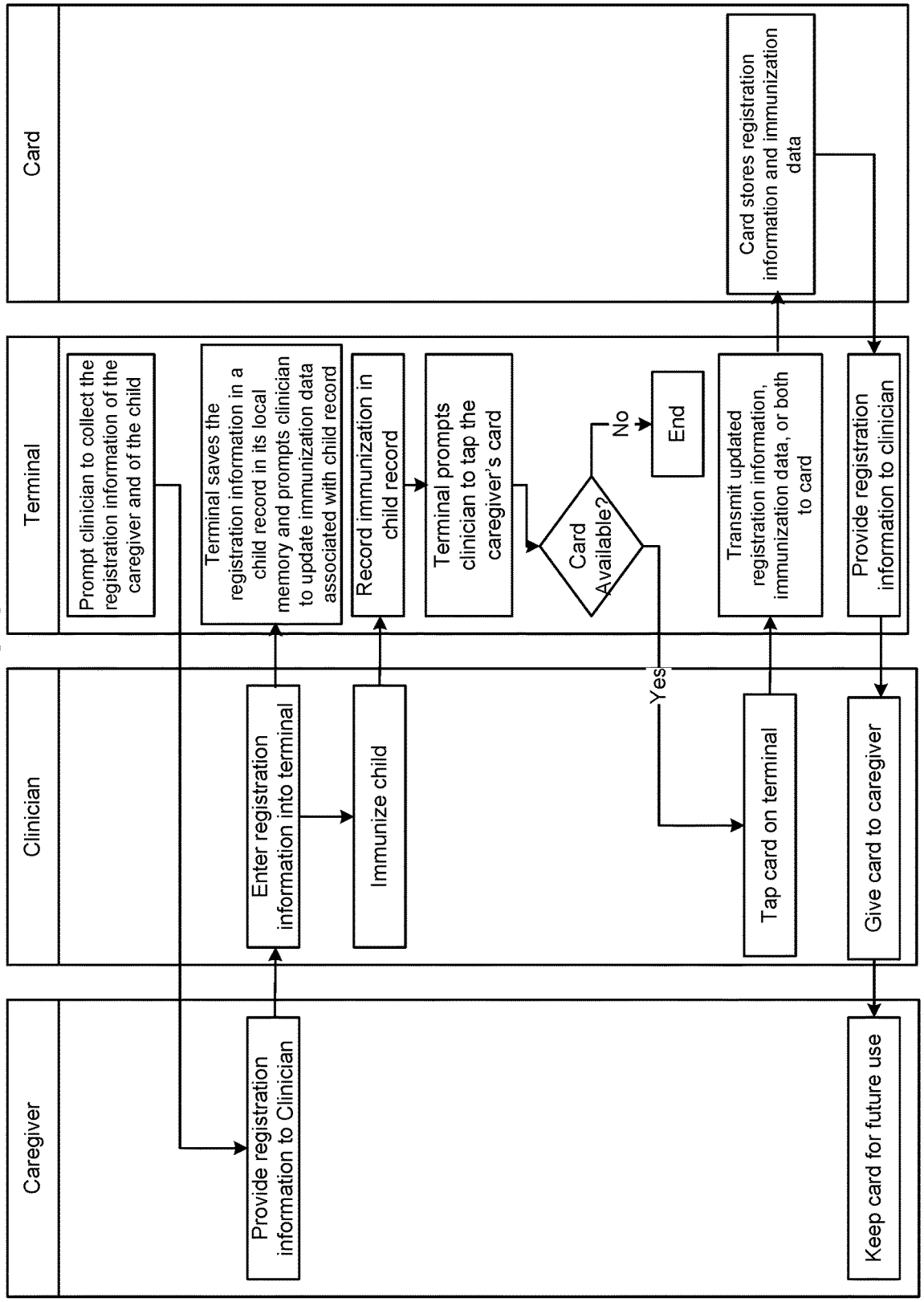

FIGS. 8A and 8B illustrate an example detailed flowchart of the functionality performed by each of the clinician, caregiver, terminal, and tracking vehicle (described in FIGS. 8A and 8B as a card) when a user and their caregiver visit a clinic for the first time and provide biometric information. The de-duplication (or de-dup) in FIG. 8A refers to determining whether biometric information provided by a user and their caregiver when they visit a clinic for the first time matches biometric data included in a user record and adjudication refers to allowing an administrator (for example, a clinician) to determine whether a user record or caregiver record associated with the user, caregiver, or both who provided their biometric information already exists. It should be noted that the flowchart of FIG. 8B is a continuation of the flowchart in FIG. 8A and that the last step in FIG. 8A is the first step in FIG. 8B. It should also be noted that the child referred to in FIG. 8A and FIG. 8B is equivalent to the user described herein.

Figure 9A:
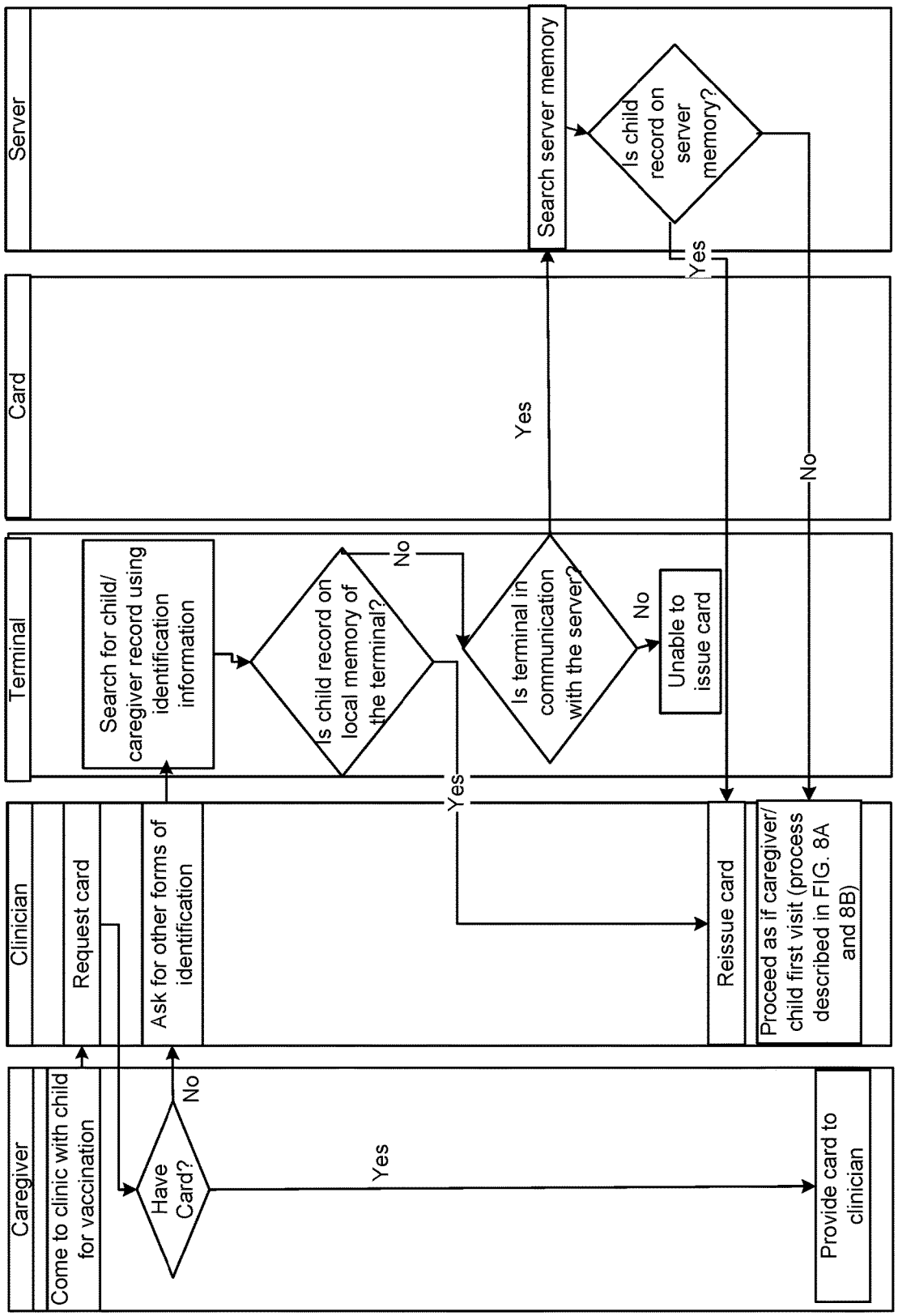
Figure 9B:
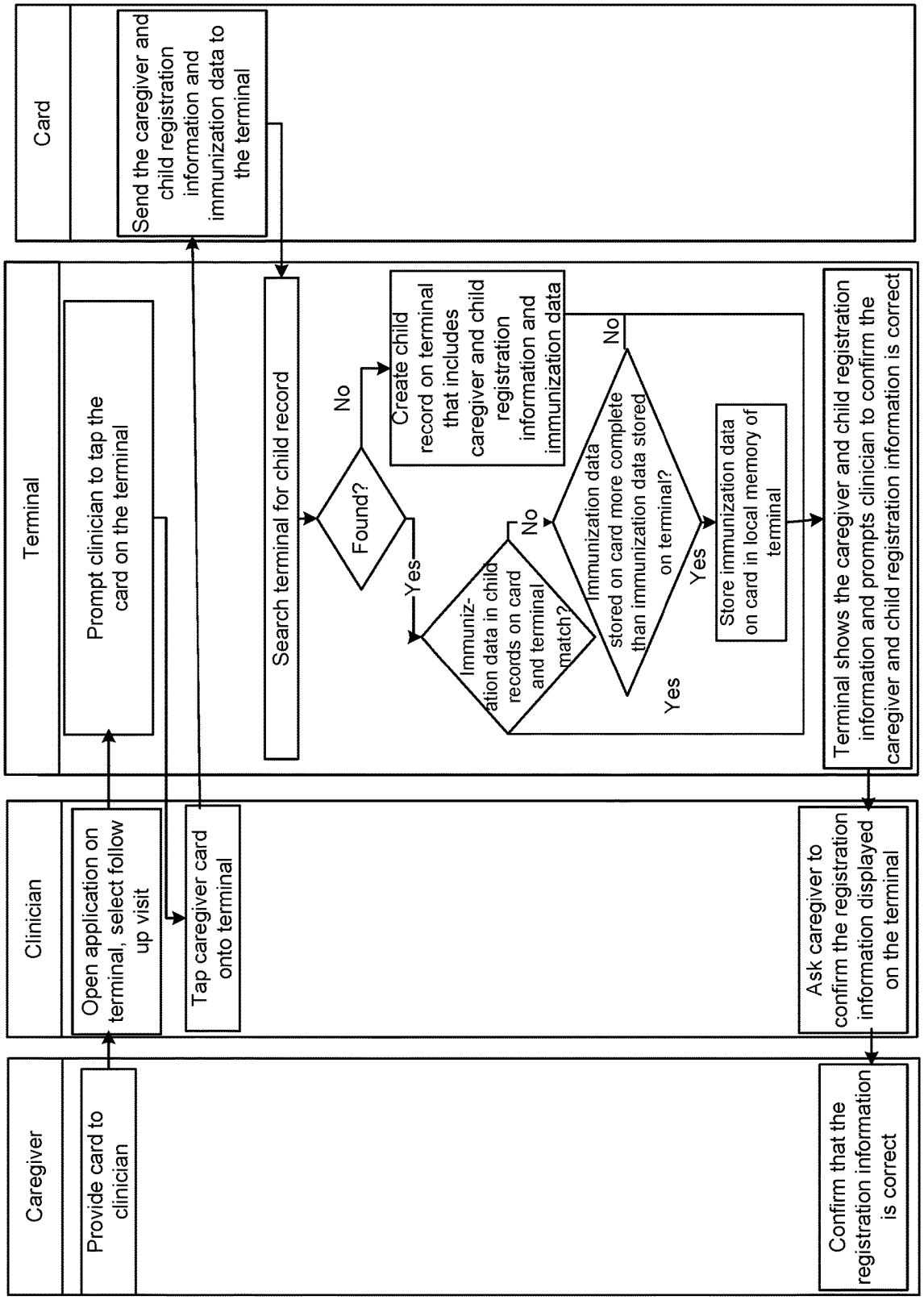
Figure 9D:
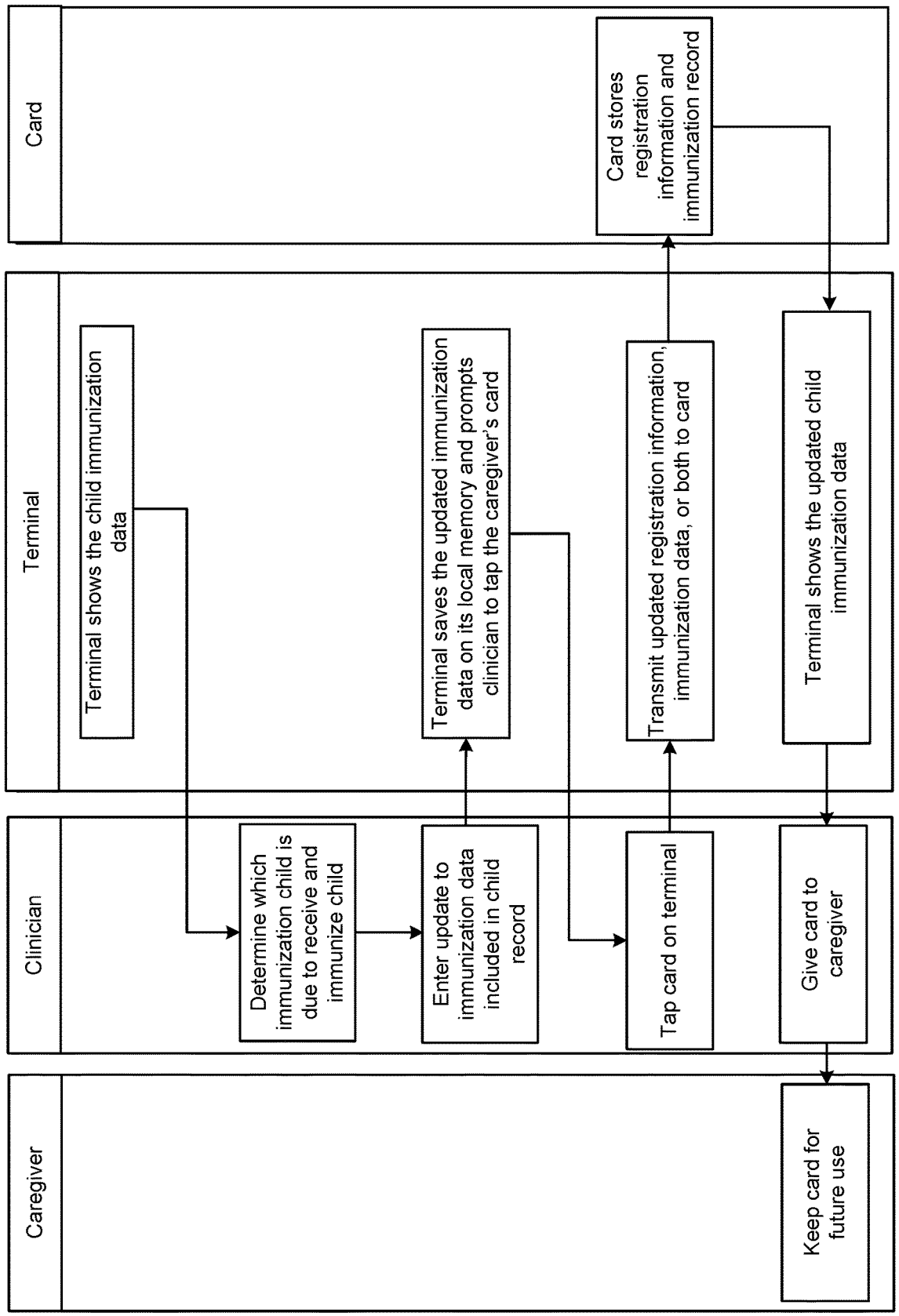

FIGS. 9A through 9D illustrate an example detailed flowchart of the functionality performed by each of the clinician, caregiver, terminal, tracking vehicle (described in FIGS. 9A through 9D as a card), and server when a user and their caregiver make a subsequent visit to a clinic but do not provide biometric information. It should be noted that the flowcharts of FIG. 9B, FIG. 9C, and FIG. 9D are continuations of the flow chart in FIG. 9A. The last step in FIG. 9A is the first step in FIG. 9B, the last step in FIG. 9B is the first step in FIG. 9C, and the last step in FIG. 9C is the first step in FIG. 9D. It should also be noted that the child and child record referred to in FIG. 9A through FIG. 9D is equivalent to the user and user record described herein.

Figure 11:
FIG. 11 illustrates an example of a vaccination stock report generated by the terminal of FIG. 2.

As mentioned above, the memory 205 of the terminal 125 also includes clinic data 245. FIGS. 10 and 11 illustrate examples of the clinic data 245 that the electronic processor 200 may be configured to track. FIG. 10 illustrates a table 1000 immunization information for a plurality of patients for which the terminal 125 stores the plurality of user records 240. In the example illustrated in FIG. 10, for each vaccination that a patient has received, a date that the vaccination was administered is recorded in the table 1000. For example, in the table 1000 the patient Kiogi, B received the Polio Oral 1 vaccination on Feb. 2, 2019. The information stored in the table 1000 may be input by a clinician via the input device 220, automatically be updated based on data received from the tracking vehicles 105-120 and the server 140, or both.

FIG. 11 illustrates a vaccination stock report 1100 that may be generated and output (via, for example, the display device 215) by the electronic processor 200 of the terminal 125. The vaccination stock report may include information regarding the number of vaccination doses available at a clinic. In one example, a clinician may input a number of doses of each type of vaccination that the clinic receives. In some embodiments, as doses are administered the terminal 125 is configured to automatically update the number of doses that the clinic has. In other embodiments, as doses are administered the clinician updates the number of doses that the clinic has via the input device 220.

Thus, embodiments described herein provide, among other things, a system for maintaining individual immunization records. Various features and advantages are set forth in the following claims.

What is claimed is:

1. A system for maintaining individual immunization records, the system comprising:
   a server including a server memory and a server electronic processor, wherein the server memory is configured to store a plurality of user records and a plurality of caregiver records;
   a tracking vehicle storing a first instance of a user record, wherein the user record includes a unique caregiver identifier and the unique caregiver identifier is associated with one or more user records and a single financial account; and
   a terminal including an electronic processor and a memory, wherein the electronic processor is communicatively connected to the memory, the electronic processor of the terminal configured to:
   communicate with the tracking vehicle;
   obtain a second instance of the user record stored in the memory of the terminal;
   determine whether immunization data in the first instance or the second instance is more recent, wherein:
   when the first instance of the user record from the tracking vehicle includes more recent immunization data than the second instance of the user record stored in the memory of the terminal, update the user record stored in the memory of the terminal with the more recent immunization data in the first instance of the user record of the tracking vehicle;
   receive updated immunization information from a clinician when the clinician provides a new immunization to the user based upon the instances of the user record from the tracking vehicle and terminal;
   update the first and second instances of the user records to reflect the new immunization;
   communicate user record updates with the server when connectivity with the server is established; and
   when the server electronic processor determines that the user record included in the memory of the terminal has been successfully stored in the server memory and at least a predetermined amount of time has passed since the last update to the user record occurred, receive a signal from the server electronic processor indicating that the user record may be deleted from the memory of the terminal.

2. The system according to claim 1, wherein the electronic processor is configured to generate a vaccination stock report.

3. The system according to claim 1, wherein the electronic processor of the terminal is further configured to:
   when the terminal is in communication with the server, receive a third instance of the user record from the server; and
   when the third instance of the user record from the server includes more recent immunization data than the second instance of the user record stored in the memory of the terminal, update the user record stored in the memory of the terminal with the more recent immunization data in the third instance of the user record from the server.

4. The system according to claim 1, wherein the terminal further includes a biometric identifier device and the electronic processor is configured to
   receive data from the biometric identifier device,
   when the data received is associated with a caregiver or a user, determine if the received data matches biometrically derived identifier information received from the tracking vehicle; and
   when the data received is associated with a clinician, determine if the received data matches biometrically derived identifier information stored in the memory of the terminal or received from the tracking vehicle.

5. A method for maintaining individual immunization records, the method comprising:
   a terminal including an electronic processor and a memory communicating with a tracking vehicle storing a first instance of a user record, wherein the user record includes a unique caregiver identifier and the unique caregiver identifier is associated with one or more user records and a single financial account;
   obtaining, with the electronic processor, a second instance of the user record stored in the memory of the terminal;
   determining, with the electronic processor, whether immunization data in the first instance or the second instance is more recent, wherein:
   when the first instance of the user record from the tracking vehicle includes more recent immunization data than the second instance of the user record stored in the memory of the terminal, updating the user record stored in the memory of the terminal with the more recent immunization data in the first instance of the user record of the tracking vehicle;

receiving updated immunization information from a clinician when the clinician provides a new immunization to the user based upon the instances of the user record from the tracking vehicle and terminal; updating the first and second instances of the user records to reflect the new immunization;

when connectivity with a server is established, communicating user record updates with the server including a server electronic processor and a server memory, wherein the server memory is configured to store a plurality of user records and a plurality of caregiver records;

and when the server electronic processor determines that the user record included in the memory of the terminal has been successfully stored in the server memory and at least a predetermined amount of time has passed since the last update to the user record occurred, receiving a signal from the server electronic processor indicating that the user record may be deleted from the memory of the terminal.

6. The method according to claim 5, the method further comprising generating a vaccination stock report.

7. The method according to claim 5, the method further comprising
when the terminal is in communication with the server, receiving a third instance of the user record from the server; and
when the third instance of the user record from the server includes more recent immunization data than the second instance of the user record stored in the memory of the terminal, updating the user record stored in the memory of the terminal with the more recent immunization data in the third instance of the user record from the server.

8. The method according to claim 5, the method further comprising
receiving data from a biometric identifier device included in the terminal;
when the data received is associated with a caregiver or a user, determining if the received data matches biometrically derived identifier information received from the tracking vehicle; and
when the data received is associated with a clinician, determining if the received data matches biometrically derived identifier information stored in the memory of the terminal or received from the tracking vehicle.

9. A non-transitory computer-readable medium with computer-executable instructions stored thereon executed by an electronic processor to perform the method maintaining individual immunization records, comprising:
a terminal including the electronic processor and the non-transitory computer-readable medium communicating with a tracking vehicle storing a first instance of a user record, wherein the user record includes a unique caregiver identifier and the unique caregiver identifier is associated with one or more user records and a single financial account;
obtaining, with the electronic processor, a second instance of the user record stored in the non-transitory computer-readable medium of the terminal;
determining, with the electronic processor, whether immunization data in the first instance or the second instance is more recent, wherein: when the first instance of the user record from the tracking vehicle includes more recent immunization data than the second instance of the user record stored in the non-transitory computer-readable medium of the terminal, updating the user record stored in the non-transitory computer-readable medium of the terminal with the more recent immunization data in the first instance of the user record of the tracking vehicle;
receiving updated immunization information from a clinician when the clinician provides a new immunization to the user based upon the instances of the user record from the tracking vehicle and terminal;
updating the first and second instances of the user record to reflect the new immunization;
when connectivity with a server is established, communicating user record updates with the server including a server electronic processor and a server memory, wherein the server memory is configured to store a plurality of user records and a plurality of caregiver records; and
when the server electronic processor determines that the user record included in the non-transitory computer-readable medium of the terminal has been successfully stored in the server memory and at least a predetermined amount of time has passed since the last update to the user record occurred, receiving a signal from the server electronic processor indicating that the user record may be deleted from the non-transitory computer-readable medium of the terminal.

10. The non-transitory computer-readable medium according to claim 9, the method further comprising generating a vaccination stock report.

11. The non-transitory computer-readable medium according to claim 9, the method further comprising
when the terminal is in communication with the server, receiving a third instance of the user record from the server; and
when the third instance of the user record from the server includes more recent immunization data than the second instance of the user record stored in the non-transitory computer-readable medium of the terminal, updating the user record stored in the non-transitory computer-readable medium of the terminal with the more recent immunization data in the third instance of the user record from the server.

12. The non-transitory computer-readable medium according to claim 9, the method further comprising
receiving data from a biometric identifier device included in the terminal,
when the data received is associated with a caregiver or a user, determining if the received data matches biometrically derived identifier information received from the tracking vehicle; and
when the data received is associated with a clinician, determining if the received data matches biometrically derived identifier information stored in the non-transitory computer-readable medium of the terminal or received from the tracking vehicle.

* * * * *